United States Patent [19]

Fischer

[11] Patent Number: 5,098,303
[45] Date of Patent: Mar. 24, 1992

[54] METHOD FOR BLEACHING TEETH

[75] Inventor: Dan E. Fischer, Sandy, Utah

[73] Assignee: Ultradent Products, Inc., Salt Lake City, Utah

[21] Appl. No.: 553,168

[22] Filed: Jul. 13, 1990

Related U.S. Application Data

[63] Continuation-in-part of Ser. No. 497,934, Mar. 22, 1990.

[51] Int. Cl.$^5$ .............................................. A61C 5/00
[52] U.S. Cl. .................................................. 433/215
[58] Field of Search ....................... 433/215, 216, 217; 424/49

[56] References Cited

U.S. PATENT DOCUMENTS

| | | | |
|---|---|---|---|
| 3,379,193 | 4/1968 | Monoghan | 424/49 |
| 3,624,909 | 12/1971 | Greenberg | 424/49 |
| 3,657,413 | 4/1972 | Rosenthal | 424/49 |
| 3,969,499 | 7/1976 | Lee, Jr. et al. | 424/52 |
| 3,988,433 | 10/1976 | Benedict | 424/53 |
| 4,032,627 | 6/1977 | Suchan et al. | 424/54 |
| 4,138,814 | 2/1979 | Weitzman | 433/215 |
| 4,251,507 | 2/1981 | Olson | 424/49 |
| 4,302,441 | 11/1981 | Mühlemann et al. | 424/48 |
| 4,376,628 | 3/1983 | Aardse | 433/217.1 |
| 4,568,536 | 2/1986 | Kronenthal et al. | 424/22 |
| 4,696,757 | 9/1987 | Blank et al. | 252/186.29 |

OTHER PUBLICATIONS

Haywood et al., "Nightguard Vital Bleaching," *Quintessence International*, vol. 20, pp. 173-176 (No. 3, 1989).
Den-Mat Corporation Advertisement for "Rembrandt Lighten Bleaching Gel in *Dental Products Report*", p. 97 (Feb. 1990).
M & M Innovations Advertisement for "Nu-Smile" Dental Bleaching System Originally Appearing in the Nov., 1989 Issue of *Dental Products Report*.
Heller, L., "Is Your Dentist Up-To-Date?" *Redbook*, pp. 20-26, at 26 (Mar. 1990).
"Tooth Bleaching," Home-Use Products, *Clinical Research Associates Newsletter*, vol. 13, Issue 7 (Jul. 1989).
"Tooth Bleaching," Home-Use Products, *Clinical Research Associates Newsletter*, vol. 13, Issue 12 (Dec. 1989).

*Primary Examiner*—John J. Wilson
*Attorney, Agent, or Firm*—Workman Nydegger & Jensen

[57] ABSTRACT

The present invention discloses high viscosity sustained release dental compositions, such as tooth bleaching or fluoride compositions, for treating tooth surfaces. For maximum results, an improved dental tray having reservoirs for holding the dental composition adjacent the desired tooth surfaces is preferably used in combination with the sustained release dental composition. The sustained release dental compositions include a high carboxypolymethylene concentration which results in very high viscosity. The high level of carboxypolymethylene makes dilution of the dental compositions from saliva difficult and time consuming so that the compositions stay within the tray reservoirs, thereby providing sustained release. The concentrated carboxypolymethylene adds a unique tackiness to the dental composition which helps retain and seal the soft tray material against the patient's teeth.

15 Claims, 2 Drawing Sheets

METHOD FOR BLEACHING TEETH

RELATED APPLICATION

This application is a continuation-in-part of copending patent application Ser. No. 07/497,934, filed Mar. 22, 1990, in the name of Dan E. Fischer and entitled "SUSTAINED RELEASE DENTAL COMPOSITIONS AND METHODS FOR TREATING TEETH SURFACES," which is incorporated herein by specific reference.

BACKGROUND

1. The Field of the Invention

The present invention relates to improved dental compositions and methods for treating teeth surfaces. More particularly, the present invention is directed to high viscosity dental compositions, such as tooth bleaching compositions, having significantly improved effectiveness and sustained release activity. The dental compositions may advantageously be used in combination with a dental tray having reservoirs for holding the dental composition located adjacent the teeth surfaces to be treated.

2. The Prior Art

Virtually all people desire white or whiter teeth. To achieve this goal, people either have veneers placed over their teeth or have their teeth chemically bleached. In the past, patients who desired to have their teeth bleached had to submit to conventional in-office bleaching techniques. This usually involved carefully placing a hydrogen peroxide solution (typically 30% $H_2O_2$) on the teeth, protecting the sensitive soft tissues with a ligated rubber dam, and applying heat to the solution. Such treatments typically last 30 minutes to 1 hour with from 4 to 10 appointments being necessary for a significant change. Only the labial surface of the 6-8 front teeth is treated.

Since its introduction in early 1989, there has been a growing interest among the dental profession in home-use tooth bleaching products and methods. A current representative technique includes: (1) making an alginate impression of the patient's teeth; (2) making a stone cast of the impression; (3) vacuum forming a tray from the cast, usually from thin (0.020-0.030 inch) hard transparent material; (4) instructing the patient to (a) place 2-3 drops of a bleaching solution into each area of each tooth to be bleached, (b) place the tray in the mouth, (3) expectorate any excess bleaching solution, (4) change the bleaching solution every 1 to 2.5 hours, and (5) remove the tray during meals. A few recommend wearing the tray during the night.

The most commonly used dental bleaching agent is 10% carbamide peroxide ($CO(NH_2)_2H_2O_2$), also called urea hydrogen peroxide, hydrogen peroxide carbamide, and perhydrol-urea. Carbamide peroxide has been recommended and prescribed by dental clinicians since the 1960's as an oral antiseptic. Tooth bleaching was a side effect of extended usage. Over the counter ("OTC") compositions of 10% carbamide peroxide are available as "Gly-Oxide" by Marion Laboratories and "Proxigel" by Reed and Carnrick.

Positive results using the foregoing technique have been reported. The effectiveness depends upon such factors as type and intensity of stain, bleaching agent contact time on teeth, and amount of available active ingredient in the bleaching agent. Because the time commitment for the actual bleaching process takes place outside the dental office, the cost for the procedure is substantially less than conventional in-office bleaching techniques. Moreover, patient discomfort associated with home-use tooth bleaching techniques both during and after treatment is reportedly less than that associated with conventional in-office bleaching.

Notwithstanding the foregoing advantages, there remain some important disadvantages to home-use bleaching products and techniques. One important disadvantage is that either the bleaching agent must be frequently replaced during the day or the treatment extend for several weeks or months. Clinical test results indicate that saliva dilution and swallowing of the bleaching agent caused the volume of agent in the tray to diminish rapidly over time, thereby decreasing the amount of active ingredient available for tooth bleaching. Test results show that after one hour, less than one-half the original volume of bleaching agent was present. Thus, existing bleaching agents should be replenished about every hour in order to be effective.

Since current home-use bleaching agents must be frequently replenished, the user necessarily ingests large volumes of the bleaching agent. In many cases, ingestion of the bleaching agent causes sore throats. Some researchers have even suggested that long term repeated ingestion of large quantities of carbamide peroxide may be carcinogenic. Therefore, patient ingestion of dental bleaching compositions should be minimized.

Many patient's daytime schedules do not permit them to constantly replenish the bleaching agent. In addition, even the suggestion of periodically replenishing the bleaching agent during the night would not be favorably received by most patient's. Because of the inconvenience of constantly replacing the dental agent, patient compliance is difficult to maintain, and since patient compliance determines the ultimate success of the treatment, the need to constantly replace the dental bleaching agent is a major inconvenience which limits the success of the treatment.

Another disadvantage with current home-use bleaching compositions and techniques is that it often takes weeks to see an observable result. Although some have reported lightening of teeth in shorter periods of time, in most cases the home-use bleaching treatment lasts from 4 to 6 weeks. Under such circumstances, patients often lose their enthusiasm for the procedure and often stop complying with the treatment regimen.

From the foregoing, it will be appreciated that what is needed in the art are improved compositions and methods for treating tooth surfaces which facilitate patient compliance, so that the ultimate purpose of the treatment is realized.

Additionally, it would be a significant advancement in the art to provide sustained release dental compositions for treating tooth surfaces which do not need to be continuously replaced so that patient compliance is enhanced.

It would be another significant advancement in the art to provide dental compositions for treating tooth surfaces which provide a more constant level of dental agent in contact with the teeth surfaces rather than periodic high and low levels of the dental agent in contact with the patient's teeth.

It would be an additional advancement in the art to provide dental compositions and methods for bleaching a patient's teeth which provide noticeable lightening in a matter of days rather than weeks.

Such dental compositions and methods for treating tooth surfaces are disclosed and claimed herein.

BRIEF SUMMARY AND OBJECTS OF THE INVENTION

The present invention is directed to high viscosity sustained release dental compositions, such as tooth bleaching or fluoride compositions, for treating tooth surfaces. An improved dental tray having reservoirs for holding the dental composition adjacent the desired tooth surfaces is preferably used in combination with the sustained release dental composition.

One currently preferred sustained release dental composition includes a dental bleaching agent, such as carbamide peroxide. The concentration of dental bleaching agent may vary depending upon its reactivity. For carbamide peroxide, for example, the currently preferred concentration range is from about 3% to about 20%, with a range from about 4% to about 15% being most preferred.

The dental bleaching agent is preferably included in a high viscosity matrix material to form the sustained release dental composition. Suitable matrix materials are preferably safe for oral use, do not readily dissolve in saliva, and do not react with the dental bleaching agent. One currently preferred high viscosity matrix material is a saturated carboxypolymethylene composition. A quantity of base is preferably added to the carboxypolymethylene composition to adjust the pH to within about 5.0 to about 7.0.

The sustained release bleaching agents within the scope of the present invention have such a high viscosity that positive pressure is needed to dispense them, gravity is not sufficient. Unlike existing low-viscosity bleaching agents, the sustained release bleaching agents cannot be dispensed drop-wise from a bottle. A syringe, squeezable tube, or other similar positive pressure dispensing device must be used to dispense the bleaching compositions within the scope of the present invention.

An improved dental tray having reservoirs for holding the dental composition adjacent the desired tooth surfaces is preferably used in combination with the sustained release dental composition. The general process for preparing dental trays is known in the art. For example, an alginate impression which registers all teeth surfaces plus gingival margin is made and a stone cast is promptly made of the impression. The reservoirs are prepared by building a layer of rigid material on the stone cast on specific teeth surfaces to be treated. A dental tray is then vacuum formed from the modified cast using conventional techniques. Once formed, the tray is preferably trimmed barely shy of the gingival margin on both buccal and lingual surfaces. The resulting tray provides a perfect fit of the patient's teeth with reservoirs or spaces located where the rigid material was placed on the stone cast.

The reservoirs may also be creatively built into trays to provide additional bleaching agent to specific teeth or teeth surfaces which need more whitening than others. It has also been found that patients may experience less tooth discomfort from tray pressures when using a tray with built in reservoirs.

Before commencing a home-use teeth bleaching treatment, it is recommended that the patient's teeth be clean and that there be no restorations with leaky margins or exposed dentin. If there are large areas of exposed dentin or if restorations are inadequate, patients can develop mild to moderately severe pain.

The amount of whitening obtained during tooth bleaching is dependent upon (1) the length of time each day the tray is worn; (2) the number of days the tray is worn; and (3) the susceptibility of the teeth to the bleaching agent. For maximum whitening, an accelerated treatment time of approximately 18-20 hours per day is recommended. The treatment schedule may be tailored to each patient's lifestyle or response to the treatment, but will usually include at least treatment during the patient's sleep. It has been found that treatment during sleep is the most productive single treatment time of the day since less mouth activity "pumps" material from the tray.

Recent experimental tests have compared one dental bleaching composition within the scope of the present invention with some commercially available dental bleaching compositions. All tested bleaching compositions had the same concentration of active ingredient (10% carbamide peroxide). The tests only examined bleaching effectiveness and did not consider increased effectiveness resulting from sustained release properties. The experimental results indicate that the present bleaching composition provides significantly greater effectiveness than the other tested bleaching compositions, irrespective of its sustained release properties. It is, therefore, an object of the present invention to provide highly effective dental bleaching compositions.

An additional object of the present invention is to provide improved compositions and methods for treating tooth surfaces which facilitate patient compliance, so that the ultimate purpose of the treatment is realized.

Another important object of the present invention is to provide sustained release dental composition for treating tooth surfaces which do not need to be continuously replaced so that patient compliance is enhanced.

Yet another significant object of the present invention is to provide sustained release dental compositions for treating tooth surfaces which provide a more constant level of dental agent in contact with the teeth surfaces rather than periodic high and low levels of the dental agent in contact with the patient's teeth thereby providing noticeable lightening of a patient's teeth in a matter of days rather than weeks.

A further important object of the present invention is to provide an improved dental tray having built in reservoirs for holding dental compositions for treating tooth surfaces which enhance the effectiveness of the dental treatment and patient comfort.

These and other objects and features of the present invention will become more fully apparent from the description which follows, or may be learned by the practice of the invention.

DETAILED DESCRIPTION OF THE PREFERRED EMBODIMENTS

Figure 1:
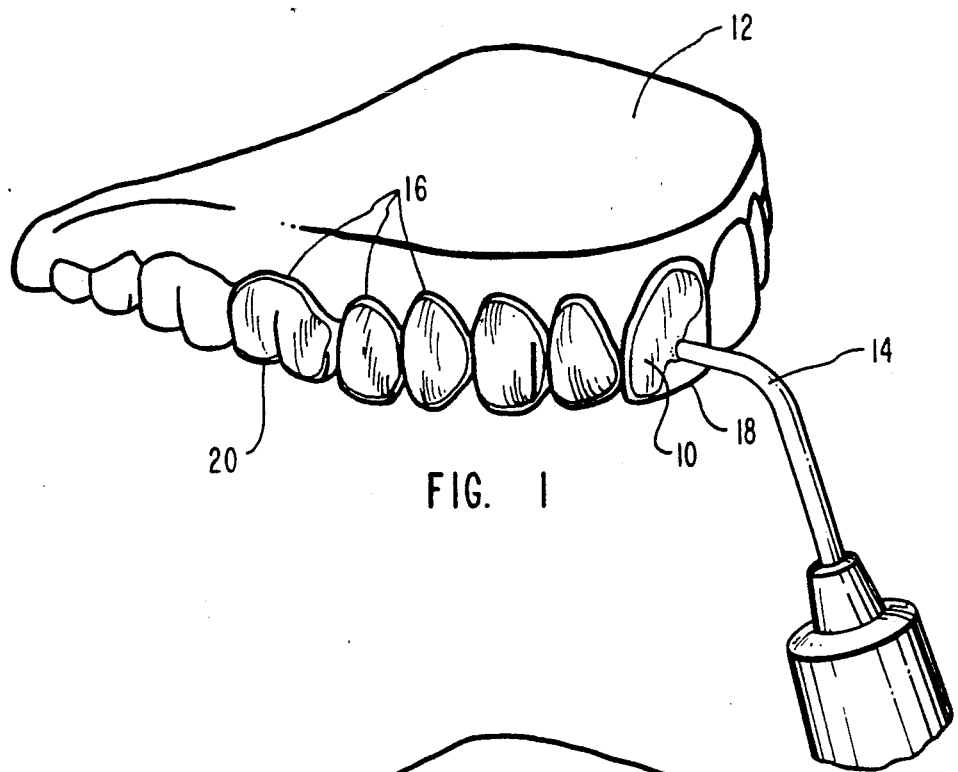
FIG. 1 is a perspective view of a stone cast of a patient's teeth with a rigid coating being applied to selected teeth surfaces.
Figure 2:
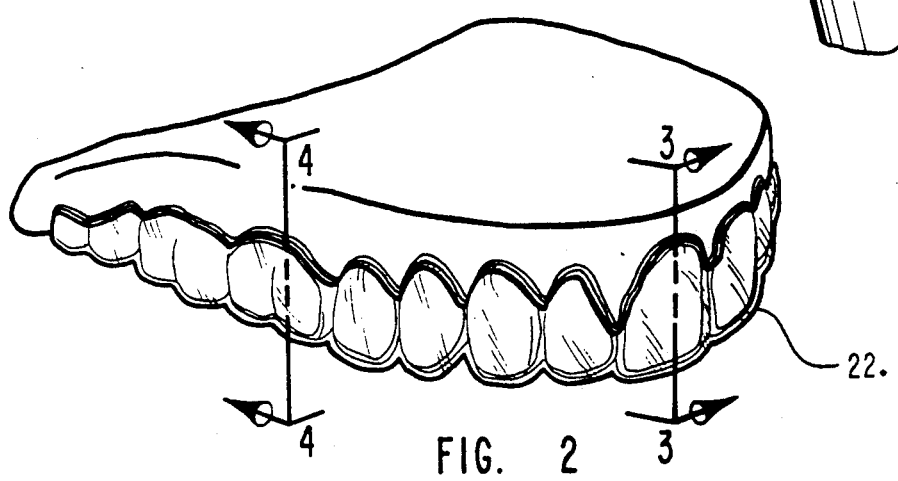
FIG. 2 is a perspective view of the stone cast of FIG. 1 with a dental tray formed from the cast and trimmed according to the teachings of the present invention.
Figure 3:
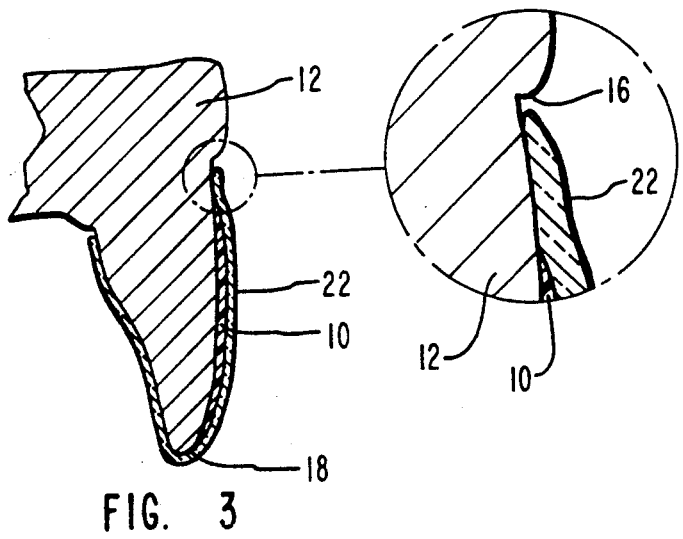
FIG. 3 is a cross-sectional view taken along line 3—3 of FIG. 2.
Figure 4:
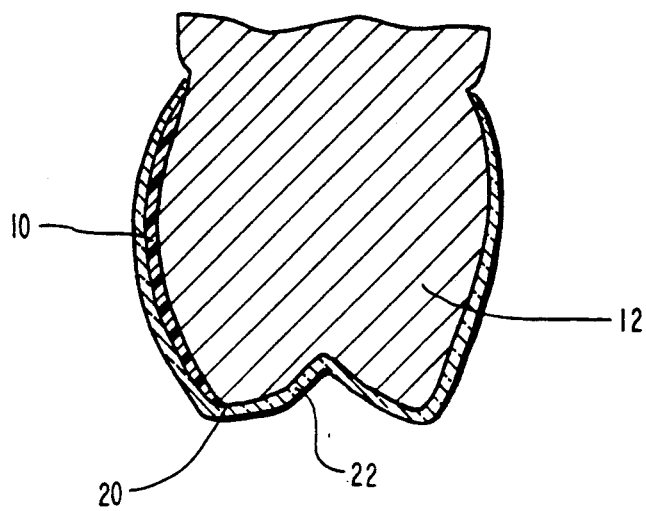
FIG. 4 is a cross-sectional view taken along line 4—4 of FIG. 2.

As summarized above, the present invention is generally related to high viscosity sustained release dental compositions, such as tooth bleaching or fluoride compositions, for treating tooth surfaces. An improved dental tray having reservoirs for holding the dental composition adjacent the desired tooth surfaces is preferably used in combination with the sustained release dental composition.

One currently preferred sustained release dental composition includes a dental bleaching agent, such as carbamide peroxide. The concentration of dental bleaching agent may vary depending upon its reactivity. For carbamide peroxide, for example, the currently preferred concentration range is from about 3% to about 20%, with a range from about 4% to about 15% being most preferred. In the case of hydrogen peroxide, which is more reactive than carbamide peroxide, the currently preferred concentration range is from about 2% to about 10%.

The dental bleaching agent is preferably included in a high viscosity matrix material to form the sustained release dental composition. Suitable matrix materials are preferably safe for oral use, do not readily dissolve in saliva, and do not react with or inactivate the dental bleaching agent. One currently preferred high viscosity matrix material is a concentrated carboxypolymethylene composition. Carboxypolymethylene is a slightly acidic vinyl polymer with active carboxyl groups. Suitable carboxypolymethylene compositions may be obtained from B. F. Goodrich Company under the trade name "carbopol".

The normal concentration of various carboxypolymethylene resins in water, according to the manufacturer, is below about 2%. Some commercially available dental bleaching compositions contain low concentrations of carbopol. Importantly, it has been found that by preparing saturated carboxypolymethylene compositions having an absolute concentration in the range from about 3.5% to about 12%, preferably from 4.5% to about 10%, suitable high viscosity, sustained release dental compositions may be prepared.

Due to the large quantities of nonaqueous components in the dental compositions within the scope of the present invention, the actual concentration of carboxypolymethylene in the total quantity of water in the dental composition will preferably be in the range from about 15% to about 35%, and most preferably from about 20% to about 30%. In some special applications where very high concentrations of carboxypolymethylene are desired, the concentration of carboxypolymethylene in the total quantity of water in the dental composition may even be as great as about 40%.

One currently preferred carboxypolymethylene composition is known as Carbopol 934P. Carbopol 934P is a high purity pharmaceutical grade of Carbopol 934, having an approximate molecular weight of about 3,000,000. In addition to thickening, suspending, and emulsifying, Carbopol 934P has been used in dry tablets to impart sustained release properties. Extensive toxicity studies have been conducted on Carbopol 934P, and a master file has been established with the Food and Drug Administration. It is listed as Carbomer 934P in the National Formulary.

It is believed other carboxypolymethylene resins, such as Carbopol 940, may be substituted for the Carbopol 934P. However, based upon clinical and laboratory evaluations, Carbopol 940 appears to dilutes faster than Carbopol 934P. In addition, Carbopol 934P is currently preferred because it is obtainable in a pharmaceutical grade. Therefore, Carbopol 934P is a currently preferred carboxypolymethylene composition.

The concentrated carboxypolymethylene compositions within the scope of the present invention have a number of important characteristics in addition to high viscosity. Enough carboxypolymethylene is added to the dental compositions beyond that required to provide high viscosity such that a significant quantity of saliva or water is required to lower the viscosity to the point that the dental agent may be diluted and washed out by saliva. Because the high level of carboxypolymethylene makes dilution from saliva difficult and more time consuming, the resulting dental compositions provide a sustained release of the dental agent.

Another important advantage of the concentrated carboxypolymethylene compositions within the scope of the present invention is that on contact with saliva, the composition becomes initially firmer. As a result, a seal around the periphery of the dental tray is formed where the composition is in contact with saliva which keeps the remainder of the composition in contact with the teeth surfaces entrapped and "sealed" therein. The firmer material at the tray periphery also fills the minor discrepancies of the tray-to-tooth fit.

In most cases, high levels of carboxypolymethylene will be preferred so that the sustained release action of the dental composition will be maintained over a greater period of time in a high salivating patient. However, in some cases it may be desireable to use lower concentrations of carboxypolymethylene, relatively speaking, but still higher than typical concentrations, so that the sustained release action will last a shorter period of time. Thus, by varying the concentration of carboxypolymethylene, some control over the period of dental agent activity may be obtained.

The concentrated carboxypolymethylene composition also has a tackiness or stickiness which retains and seals the thin soft tray material against the teeth thereby preventing migration of the composition out of the tray. The tackiness of the composition not only keeps the composition within the reservoirs, but also retains the tray against the patient's teeth, thereby permitting softer, thinner, and more flexible tray materials to be used. It has been found that if too much carboxypolymethylene is used, the tackiness can decrease and the composition encumbers complete tray insertion.

In order to obtain a concentrated carboxypolymethylene composition, it is recommended that the carboxypolymethylene be mixed with a quantity of glycerine before attempting to disperse it in water. The glycerine enables the large quantities of carboxypolymethylene to be dispersed easier in water. It has also been observed that once the carboxypolymethylene and glycerine are mixed, it is important to quickly disperse the mixture in the water or else it becomes an unmanageable solid. It is recommended that the concentration of glycerine in the final sustained release dental composition be in the range from about 20% to about 70% by weight, and preferably in the range from about 40% to about 60% by weight.

In addition to functioning as a humectant, the glycerine also provides some flavor sweetening enhancement such that a bland flavor is perceived. A few possible substitutes for glycerine include polypropylene, sorbitol, some polyethylene glycols or other polyols.

It is currently preferred that the amount of water in the sustained release dental composition be in the range from about 10% to about 60% by weight, and preferably in the range form about 15% to about 40% by weight. It will be appreciated that the quantity of water in the total dental composition may come from different sources. For instance, the dental bleaching agent and base, discussed below, may come as aqueous solutions.

Because carboxypolymethylene is a polycarboxylic acid, it tends to lower the pH of the resulting bleaching composition. It appears, based upon clinical and in vitro testing, that dental compositions with a pH below about 5 are able to etch enamel. To avoid etching enamel, it is currently preferred to have the pH of the sustained release bleaching composition in the range from about 5 to about 7. This is most easily accomplished by adding a base to the composition to adjust the pH. Inorganic and organic bases may be used; the use concentrated sodium hydroxide (50% NaOH) is one currently preferred embodiment. Although it is possible to use lower concentrations of sodium hydroxide or other bases, such as triethanolamine, there is a risk that the lower concentrations may dilute the dental composition and affect its viscosity or sustained release characteristics.

An important characteristic of the high viscosity, sustained release dental compositions within the scope of the present invention is that the compositions are still observed, from a clinical standpoint, after about 3 to 7 hours of normal daytime activity and after about 7 to 10 hours of sleep. That is, the sticky, high viscosity dental composition is still observable in the dental tray after an extended period of time, such as at the end of the night.

Unlike existing low-viscosity bleaching agents which are placed drop-by-drop into the tray, the sustained release bleaching agents within the scope of the present invention have such a high viscosity that they cannot be dispensed dropwise into the tray from a bottle. Positive pressure is needed to expel the sustained release bleaching agents of the present invention, gravity is not sufficient.

One currently preferred method of dispensing the bleaching agent uses a syringe. Squeezable tubes and other similar dispensing devices may also be used to dispense the bleaching agent. Upon dispensing, the sustained release bleaching agent is sufficiently viscous that it does not settle or spread when dispensed, but remains as a single extruded strand of bleaching agent.

It is currently preferred to provide a unit dose of the dental agent in a syringe or similar dispensing device. In this way, the patient can load the precise amount of dental agent onto the dental tray for each treatment period. By using such dispensing devices, the dentist is also able to monitor and control hoe many doses the patient has received and used.

An improved dental tray having reservoirs for holding the dental composition adjacent the desired tooth surfaces is preferably used in combination with the sustained release dental composition. The general process for preparing dental trays is known in the art. For example, an alginate impression which registers all teeth surfaces plus gingival margin is made and a stone cast is promptly made of the impression. Excess stone is trimmed away for ease of manipulation and forming of the plastic tray.

Reference is now made to FIGS. 1-4. The present invention modifies known procedure by applying a thin coating 10 of rigid material to stone cast 12 over the teeth surfaces to be treated. As shown in FIG. 1, coating 10 may be conveniently applied using a syringe applicator 14. The coating may be also light cured for convenience. Care is taken to ensure that coating 10 is kept a distance greater than about 1 mm from gingival line 16 and preferably kept from about 1¼ mm to about 1½ mm from gingival line 16. The finished coating is preferably about ½ mm thick. It is particularly important when applying the rigid coating material to not cover over incisal edges 18 and occlusal edges 20. These edges should contact the finished tray to prevent vertical movement of the tray during use which could act as a pump by expressing out the bleaching agent and sucking in saliva.

A dental tray 22 is then vacuum formed from the modified cast using conventional techniques. Tray 22 is preferably constructed of soft transparent vinyl material having a preformed thickness from about 0.035 inch to about 0.06 inch. Soft material is more comfortable for the patient to wear. Most patient's will find 0.035 inch to be suitable. It will be appreciated that the final tray thickness may vary depending on the technique used to prepare the tray. Patient's suspected of being bruxers or hard biters may require a 0.06 inch tray material. Of course, patients should be counselled to not eat with trays in place or to bite firmly into them. In extreme cases, a thicker or harder plastic may be necessary.

Once formed, tray 22 is preferably trimmed barely shy of gingival margin 16 on both buccal and lingual surfaces. Enough tray material should be left to assure that all of the tooth will be covered to within about ¼ mm to about ⅓ mm of the gingival border upon finishing and beveling of the tray periphery. It is also important to scallop up and around interdental papilla so that the finished tray does not cover them. All tray edges are preferably smoothed so that the lip and tongue will not feel an edge prominence. Slight adjustments to the tray may be made by carefully heating and stretching the tray material.

From practice, it has been found that patients may experience less tooth discomfort from tray pressures when using a tray with reservoirs built into the tray as described above. It is currently believed this is due to the fact that the teeth are not held as firmly by the tray, so "orthodontic" pressures experienced by teeth from tray indiscrepancies are minimized. The use of thin, soft tray materials further minimizes these "orthodontic" forces, compared to the harder plastics currently used in the art.

Reservoirs may also be creatively built into trays to provide additional bleaching agent to one or more teeth of an arch needing more whitening than others or to selected parts of a tooth needing more whitening than other parts.

To achieve most rapid results, it is recommended to use sustained release bleaching agent within the scope of the present invention in combination with the trays incorporating reservoirs. Nevertheless, it has been observed that bleaching occurs much more rapidly using conventional trays with sustained release bleaching compositions of the present invention than with existing bleaching agents. In addition, some increase is effectiveness has also been observed when using existing bleaching agents with trays incorporating reservoirs than with conventional trays without reservoirs.

Before commencing a home-use teeth bleaching treatment, it is recommended that the patient's teeth be clean of calculus and external stains. Restorations should be water tight and all dentin, particularly gingival dentin with potential or existing sensitivities, should be covered. It has been observed that exposed root surfaces may experience sensitivity from sustained release bleaching agent within the scope of the present invention. In many cases dentin may be covered with a layer of dentin bonding agent or sealant to prevent this.

Since most patients will want to complete their treatment as soon as possible, recommended treatment times start at approximately 18-20 hours a day. Patients are instructed to insert the tray loaded with fresh bleaching agent after each meal and before going to bed for most rapid results. Gum soreness or other patient discomfort has been reported more often for such accelerated treatment schedules that go longer than one to two days.

A second possible treatment schedule is to allow a break-time to occur between dinner and bed. This allows the patient to participate in evening social functions without wearing the tray. In addition, oral tissues are allowed to rest during the break-time.

Another recommended treatment schedule, particularly for those where the treatment may require more than one or two days, is to load and insert the tray only before bed and after lunch. This gives the teeth and soft tissues a rest for approximately two 4-5 hour intervals between the two longer treatment periods. Potential soreness is most often prevented this way and treatment time may only be extended 20% to 30% over the more accelerated treatment schedules.

Finally, for those patients who are often in public or those who have experienced moderate or greater problems of soreness, it is recommended that the tray be worn only at night. During sleep is the most productive single treatment time since less mouth activity "pumps" material from the tray.

Regardless of which treatment schedule is used, the use of sustained release dental bleaching compositions within the scope of the present invention provides a more constant level of bleaching agent adjacent the teeth than existing home-use bleaching systems. Even if patient compliance with existing home-use dental bleaching systems is such that fresh bleaching agent is added every hour, there still would be periodic high and low levels of bleaching agent adjacent the teeth. Since the amount and length of time the active bleaching agent is adjacent the teeth significantly influences the efficiency of the treatment, the sustained release bleaching compositions and methods of the present invention represent a significant improvement over existing home-use dental bleaching systems.

If patient instructions are followed, more predictable results are obtained in days rather than weeks. Also, less total volume of bleaching agent is used (from 1/10 to 1/20 the volume of conventional peroxide solutions). As a result, less bleaching agent is swallowed by the patient.

At the end of the bleaching treatment, a sustained release fluoride composition may optionally be administered to the patient. For convenience, the same tray may be used to treat the teeth with fluoride as was used to bleach the teeth. Such fluoride treatment regimens may include 2 to 4 three hour treatments, or 1 or 2 night-time treatments. One typical sustained release fluoride composition within the scope of the present invention contains 0.5% sodium fluoride in a high viscosity gel.

The following examples set forth various sustained release dental compositions within the scope of the present invention. These examples are intended to be purely exemplary and should not be viewed as limiting the scope of the present invention.

EXAMPLE 1

A sustained release dental bleaching composition within the scope of the present invention was prepared by combining the following ingredients:

| Ingredient | Weight | Weight % |
|---|---|---|
| Carbamide peroxide | 13.2 gm | 10% |
| Water | 27.5 gm | 21% |
| Glycerine | 74.6 gm | 57% |
| Carbopol 934P | 9.5 gm | 7% |
| Sodium hydroxide (50%) | 6.5 gm | 5% |

The Carbopol 934P was obtained from B.F. Goodrich Company, Cleveland, Ohio. The carbopol was combined with the glycerine and then quickly mixed with the water. The glycerine enables the carbopol to be dispersed in the water. The carbamide peroxide was dissolved in the water before the glycerine-carbopol mixture was added to the water. The foregoing composition had a percentage of carbopol in water of about 25.7%. The sodium hydroxide was gradually blended into the homogeneous composition in order to raise the pH to an acceptable level.

The foregoing procedure produced in a sustained release dental bleaching composition which was placed in a dental tray such as that described in connection with FIGS. 1-4 and worn by a patient for 9 hours. Subsequent examination of the patient's teeth indicated that the teeth had whitened 1-1.5 units on a Vita shade guide and that significant quantities of the sustained release bleaching composition was still observed in the application tray.

EXAMPLE 2

A sustained release dental bleaching composition within the scope of the present invention was made according to the procedure of Example 1, except that the ingredients were combined in the following amounts:

| Ingredient | Weight | Weight % |
|---|---|---|
| Carbamide peroxide | 1150 | 10 |
| Water | 2030 | 18 |
| Glycerine | 6660 | 59 |
| Carbopol 934P | 830 | 7 |
| Sodium hydroxide | 650 | 6 |

The foregoing procedure resulted in a sustained release dental bleaching composition. The foregoing composition has a percentage of carbopol in water of about 25.6%. The composition possessed a high viscosity and excellent sustained release teeth bleaching activity.

EXAMPLE 3

A sustained release dental bleaching composition within the scope of the present invention is made according to the procedure of Example 1, except that the ingredients are combined in the following amounts:

| Ingredient | Weight Percent |
| --- | --- |
| Carbamide peroxide | 20 |
| Water | 20 |
| Glycerine | 40 |
| Carbopol 934P | 12 |
| Sodium hydroxide | 8 |

The foregoing procedure results in a sustained release dental bleaching composition. The foregoing composition has a percentage of carbopol in water of about 37.5%. The composition possesses a high viscosity and excellent sustained release teeth bleaching activity.

EXAMPLE 4

A sustained release dental bleaching composition within the scope of the present invention is made according to the procedure of Example 1, except that the ingredients are combined in the following amounts:

| Ingredient | Weight Percent |
| --- | --- |
| Carbamide peroxide | 5 |
| Water | 20 |
| Glycerine | 60 |
| Carbopol 934P | 10 |
| Sodium hydroxide | 5 |

The foregoing procedure results in a sustained release dental bleaching composition. The foregoing composition has a percentage of carbopol in water of about 33.3%. The composition possesses a high viscosity and excellent sustained release teeth bleaching activity.

EXAMPLE 5

A sustained release dental bleaching composition within the scope of the present invention is made according to the procedure of Example 1, except that the ingredients are combined in the following amounts:

| Ingredient | Weight Percent |
| --- | --- |
| Carbamide peroxide | 10 |
| Water | 40 |
| Glycerine | 30 |
| Carbopol 934P | 12 |
| Sodium hydroxide | 8 |

The foregoing procedure results in a sustained release dental bleaching composition. The foregoing composition has a percentage of carbopol in water of about 23.1%. The composition possesses a high viscosity and excellent sustained release teeth bleaching activity.

EXAMPLE 6

A sustained release dental bleaching composition within the scope of the present invention is made according to the procedure of Example 1, except that the ingredients are combined in the following amounts:

| Ingredient | Weight Percent |
| --- | --- |
| Carbamide peroxide | 18 |
| Water | 15 |
| Glycerine | 60 |
| Carbopol 934P | 4 |
| Sodium hydroxide | 3 |

The foregoing procedure results in a sustained release dental bleaching composition. The foregoing composition has a percentage of carbopol in water of about 21.1%. The composition possesses a high viscosity and excellent sustained release teeth bleaching activity.

EXAMPLE 7

A sustained release dental bleaching composition within the scope of the present invention is made according to the procedure of Example 1, except that the ingredients are combined in the following amounts:

| Ingredient | Weight Percent |
| --- | --- |
| Carbamide peroxide | 14 |
| Water | 10 |
| Glycerine | 70 |
| Carbopol 934P | 3.5 |
| Sodium hydroxide | 2.5 |

The foregoing procedure results in a sustained release dental bleaching composition. The foregoing composition has a percentage of carbopol in water of about 25.9%. The composition possesses a high viscosity and excellent sustained release teeth bleaching activity.

EXAMPLE 8

A sustained release dental bleaching composition within the scope of the present invention is made according to the procedure of Example 1, except that the ingredients are combined in the following amounts:

| Ingredient | Weight Percent |
| --- | --- |
| Carbamide peroxide | 5 |
| Water | 60 |
| Glycerine | 20 |
| Carbopol 934P | 10 |
| Sodium hydroxide | 5 |

The foregoing procedure results in a sustained release dental bleaching composition. The foregoing composition has a percentage of carbopol in water of about 14.3%. The composition possesses a high viscosity and excellent sustained release teeth bleaching activity.

EXAMPLE 9

A sustained release dental fluoride composition within the scope of the present invention was prepared by combining the following ingredients:

| Ingredient | Weight | Weight Percent |
| --- | --- | --- |
| Sodium fluoride | 52 gm | 1.1% |
| Water | 1000 gm | 21.5% |
| Glycerine | 2980 gm | 64.1% |
| Carbopol 934P | 380 gm | 8.2% |
| Sodium hydroxide (50%) | 238 gm | 5.1% |

The foregoing ingredients are mixed according to the procedure of example 1, except that sodium fluoride is used instead of carbamide peroxide. The fluoride concentration is preferably maintained about 1.1% so that the free fluoride ion concentration is about 0.5%. The foregoing composition has a percentage of carbopol in water of about 27.5%. The foregoing procedure produces a sustained release dental fluoride composition suitable for use with a dental tray such as that described in connection with FIGS. 1–4.

EXAMPLE 10

In this example, the in vitro brightening effect of two commercially available bleaching agents was measured and compared with the dental bleaching composition prepared according to the procedure of Example 1. Thirty-six (36) extracted anterior and premolar teeth without caries or restorations were randomly divided into four (4) groups and mounted. A thermoplastic splint was made for each group. In addition to the dental bleaching agent of Example 1, Denta-Lite (manufactured by Challenge Products, Osage Beach, MO) and Proxigel (manufactured by Reed P Carnrick, Piscataway, (N.J.) were tested. All of bleaching agents contained 10% carbamide peroxide as the active ingredient. Groups 1-3 were treated with the bleaching agents and group 4 was used as a control and bathed in sterile distilled water.

Bleaching agent was placed into a splint and replaced every 3 hours during the day and after 8 hours at night. The treatment continued for a period of 2 weeks averaging a minimum of 18 hours of bleaching per day. All teeth and splints were brushed and rinsed with water before replacing bleaching agents.

Measurements were taken using a Pentax photo spot meter, measuring brightness changes occurring at intervals of 24 hours, 72 hours, 7 days, and 14 days. The photo spot meter was equipped with an analog meter and the ability to read in 0.1 value variations. The meter was attached to a measuring apparatus which reflected two light sources at a 60 degree deflection angle toward the crown of the tooth being measured. A rheostat controlled the light sources to allow a constant emittance during each measurement. The data were analyzed using a 2-way ANOVA and Duncan's multiple range test.

Photographs were taken before, at 72 hours, and at 14 days following bleaching. A 35 mm single reflex camera with a macro lens and a 2× diopter was used for all photography.

Figure 5:
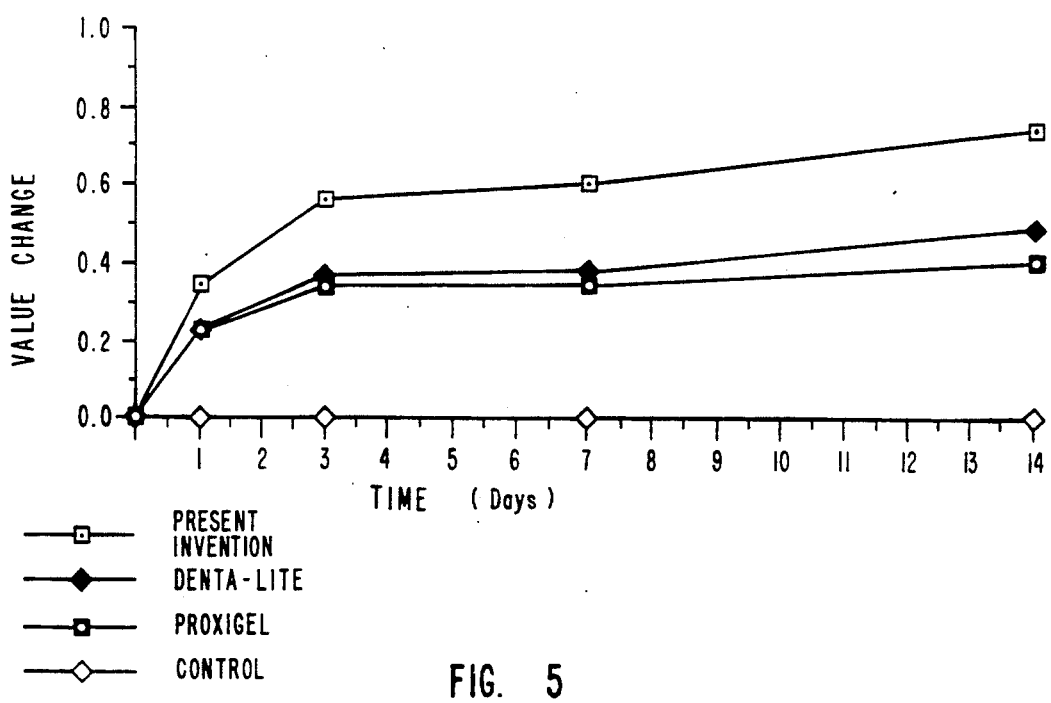
FIG. 5 is a graph illustrating the results of Example 10.

The results of this Example are reported in Table 1 and illustrated graphically in FIG. 5. They indicate that the dental bleaching composition within the scope of the present invention is over 50% more effective than the two commercially available dental bleaching agents having the same concentration of active ingredient. In fact, the bleaching agent of Example 1 provided greater whitening in just 3 days of treatment than the other bleaching agents did after two weeks of treatment.

It is important to recognize that the results of this Example to not address the impact of saliva on the effectiveness of the dental bleaching agents. The sustained release characteristics of the dental bleaching agent within the scope of the present invention were not addressed by this Example. Therefore, the effectiveness of the present invention can be expected to be even greater than the prior art bleaching agents when the sustained release activity is considered.

TABLE 1

Bleaching Effect of 10% Carbamide Peroxide
Value Changes: Means and standard deviations

| Bleaching Agent | No. | 24 Hrs. | 72 Hrs. | 7 Days | 14 Days |
|---|---|---|---|---|---|
| Water | 9 | 0 | 0 | 0 | 0 |
| Example 1 | 9 | .34 (.06) | .56 (.08) | .60 (.09) | .67 (.13) |
| Denta-Lite | 9 | .22 (.08) | .35 (.11) | .38 (.10) | .48 (.13) |
| Proxigel | 9 | .22 (.07) | .33 (.12) | .34 (.11) | .40 (.10) |

Although much of the foregoing discussion has focused on sustained release dental bleaching or fluoride compositions, it will be appreciated that other dental compositions, whether sustained release or not, may also be prepared and used within the scope of the present invention. For instance, anticariogenic agents such as chlorhexidine gluconate and antimicrobial agents for treating periodontal pockets such as tetracycline may be incorporated into sustained release compositions. When the such dental compositions are for treating soft tissues, the preferred tray design may need to be altered so that the tray overlaps the patient's gums.

In some cases, the dental agents may be used without a dental tray. For example, a sustained release dental composition having an antimicrobial agent may be expressed directly into periodontal pockets. In such compositions, it would be preferred to maximize the carboxypolymethylene concentration so that the effects of saliva dilution are minimized. In addition, mucosal adhesive materials may be added to the composition to further assist in retaining the composition within the periodontal pocket. Sustained release action may last from hours to days, depending on the patient's oral and salival activity.

From the foregoing, it will be appreciated the present invention provides improved compositions and methods for treating tooth surfaces which facilitate patient compliance, so that the ultimate purpose of the treatment is realized.

Additionally, it will be appreciated that the present invention further provides sustained release dental compositions for treating tooth surfaces which do not need to be continuously replaced so that patient compliance is enhanced. The present invention also provides sustained release dental compositions for treating tooth surfaces which permit a more constant level of the dental agent to be in contact with the teeth surfaces rather than periodic high and low levels of the dental agent in contact with the patient's teeth.

It will be further appreciated that the present invention provides dental compositions and methods for bleaching a patient's teeth which provide noticeable lightening in a matter of days rather than weeks.

In addition, it will be appreciated that the present invention provides an improved dental tray having built in reservoirs for holding dental compositions for treating tooth surfaces which enhance the effectiveness of the dental treatment and patient comfort.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for bleaching a patient's teeth comprising:
   (a) obtaining a dental tray configured to cover a patient's teeth surfaces to be bleached and configured to hold a quantity of dental bleaching composition;
   (b) placing a quantity of dental bleaching composition within the dental tray, said dental bleaching composition comprising:
      a quantity of dental bleaching agent capable of bleaching vital tooth surfaces in contact with said dental bleaching agent; and
      a matrix material into which the dental bleaching agent is dispersed, said matrix material including carboxypolymethylene in the range from about 3.5% to about 12% by weight of the dental bleaching composition;
   (c) positioning the dental tray over the patient's teeth surfaces such that a portion of the dental bleaching composition is in contact with the patient's teeth surfaces to be bleached;
   (d) allowing the dental tray to remain positioned over the patient's teeth surfaces; and
   (e) removing the dental tray from the patient's teeth.

2. A method for bleaching a patient's teeth as defined in claim 1, wherein the step of obtaining a dental tray further comprises obtaining a dental tray constructed with reservoirs for holding additional dental bleaching composition such that when the dental tray is positioned over the patient's teeth surfaces, the additional dental bleaching composition within the reservoirs is in contact with the patient's teeth surfaces to be bleached.

3. A method for bleaching a patient's teeth as defined in claim 1, further comprising the step of repeating steps (b) through (e).

4. A method for bleaching a patient's teeth as defined in claim 1, wherein the quantity of dental bleaching composition placed within the dental tray includes a matrix material comprising carboxypolymethylene in the range from about 4.5% to about 10% by weight of the dental bleaching composition.

5. A method for bleaching a patient's teeth as defined in claim 1, wherein the quantity of dental bleaching composition placed within the dental tray includes a matrix material comprising carboxypolymethylene in the range from about 6% to about 8% by weight of the dental bleaching composition.

6. A method for bleaching a patient's teeth as defined in claim 1, wherein the quantity of dental bleaching composition placed within the dental tray includes a matrix material comprising carboxypolymethylene in the range from about 15% to about 35% by weight of the total quantity of water in the total dental bleaching composition.

7. A method for bleaching a patient's teeth as defined in claim 1, wherein the quantity of dental bleaching composition placed within the dental tray includes a matrix material comprising carboxypolymethylene in the range from about 20% to about 30% by weight of the total quantity of water in the total dental bleaching composition.

8. A method for bleaching a patient's teeth as defined in claim 1, wherein the quantity of dental bleaching composition placed within the dental tray includes a carbamide peroxide as the dental bleaching agent in the range from about 3% to about 20% by weight of the dental bleaching composition.

9. A method for bleaching a patient's teeth as defined in claim 1, wherein the quantity of dental bleaching composition placed within the dental tray includes a carbamide peroxide as the dental bleaching agent in the range from about 4% to about 15% by weight of the dental bleaching composition.

10. A method for bleaching a patient's teeth as defined in claim 1, wherein the dental tray remains positioned over a patient's teeth for a period of time greater than about 3 hours and wherein the dental bleaching composition remains active while the dental tray is positioned over the patient's teeth surfaces.

11. A method for bleaching a patient's teeth as defined in claim 1, wherein the dental tray remains positioned over a patient's teeth for a period of time greater than about 5 hours and wherein the dental bleaching composition remains active while the dental tray is positioned over the patient's teeth surfaces.

12. A method for bleaching a patient's teeth as defined in claim 1, wherein the dental tray remains positioned over a patient's teeth for a period of time greater than about 8 hours and wherein the dental bleaching composition remains active while the dental tray is positioned over the patient's teeth surfaces.

13. A method for bleaching a patient's teeth as defined in claim 1, wherein the quantity of dental bleaching composition placed within the dental tray is sufficiently tacky to retain the dental tray positioned against the patient's teeth surfaces.

14. A method for bleaching a patient's teeth as defined in claim 1, wherein the quantity of dental bleaching composition placed within the dental tray becomes firmer upon contact with saliva.

15. A method for bleaching a patient's teeth as defined in claim 1, wherein during the positioning step, a portion of the dental bleaching composition extends to the edge of the dental tray and forms a seal upon contact with saliva.

* * * * *

UNITED STATES PATENT AND TRADEMARK OFFICE
CERTIFICATE OF CORRECTION

PATENT NO. : 5,098,303

DATED : March 24, 1992

INVENTOR(S) : DAN E. FISCHER

It is certified that error appears in the above-identified patent and that said Letters Patent is hereby corrected as shown below:

```
Column 1, line 48, "(3)" should be --(5)--
Column 1, line 49, "(4)" should be --(6)--
Column 1, line 50, "(5)" should be --(7)--
Column 2, line 33, "patient's" should be --patients--
Column 3, line 34, before "gravity" insert --since--
Column 6, line 2, "dilutes" should be --dilute--
Column 6, line 33, "desireable" should be --desirable--
Column 7, line 41, before "gravity" insert --since--
Column 7, line 55, "hoe" should be --how--
Column 8, line 21, "patient's" should be --patients--
Column 8, line 14, "Patient's" should be --Patients--
Column 13, line 52, "to not address" should be --do not address--
Column 14, line 18, delete "the"
```

Signed and Sealed this

Nineteenth Day of January, 1993

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 5,098,303
DATED : March 24, 1992
INVENTOR(S) : Dan E. Fischer

It is certified that error appears in the above-indentified patent and that said Letters Patent is hereby corrected as shown below:

At Col. 2, line 12, delete "extend" and insert therefor -- extended--;
    at line 29, delete "patient's" and insert therefor --patient's--

At Col. 3, line 33, after "them" delete "," and insert therefor --;--.

At Col. 4, line 34, delete "composition" and insert therefor --compositions--.

At Col. 5, line 68, after "substituted for" delete "the".

At Col. 7, line 6, delete "form" and insert therefor --from--;
    at line 20, after "the use" insert --of--;
    at line 41, after "invention" delete "," and insert therefor --;--.

At Col. 8, line 24, delete "Patient's" and insert therefor --Patients--;
    at line 24, delete "breixers" and insert therefor --bruxers--;
    at line 57, delete "agent" and insert therefor --agents--;
    at line 63, after "increased" delete "is" and insert therefor --in--;
    at line 65, after "reservoirs" insert --rather--.

At Col. 10, line 32, after "produced" delete "in".

At Col. 12, line 60, capitalize "example";
    at line 62, after "maintained" insert --at--.

UNITED STATES PATENT AND TRADEMARK OFFICE
CERTIFICATE OF CORRECTION

PATENT NO. : 5,098,303

DATED : March 24, 1992

INVENTOR(S) : Dan E. Fischer

It is certified that error appears in the above-indentified patent and that said Letters Patent is hereby corrected as shown below:

Column 14, line 33, after "appreciated" insert --that--

Signed and Sealed this

Twelfth Day of September, 1995

Attest:

BRUCE LEHMAN

Attesting Officer

Commissioner of Patents and Trademarks